United States Patent [19]

Stockhausen

[11] Patent Number: 4,611,486
[45] Date of Patent: Sep. 16, 1986

[54] METHOD AND APPARATUS FOR MEASURING AND/OR MONITORING THE SURFACE TENSION OF A FLUID

[75] Inventor: Norbert Stockhausen, Munich, Fed. Rep. of Germany

[73] Assignee: Fogra Deutesche Forschungsgesselschaft fur Druck-und Reproduktionstechnik e.v., Munich, Fed. Rep. of Germany

[21] Appl. No.: 708,357

[22] Filed: Mar. 4, 1985

[30] Foreign Application Priority Data

Mar. 23, 1984 [DE] Fed. Rep. of Germany ....... 3410778

[51] Int. Cl.[4] ............................................. G01N 13/02
[52] U.S. Cl. ....................................................... 73/64.4
[58] Field of Search ........................................... 73/64.4

[56] References Cited

FOREIGN PATENT DOCUMENTS 8302500 6/1983 World Int. Prop. O. .......... 73/64.4
482656 12/1975 U.S.S.R. ............................... 73/64.4

*Primary Examiner*—Stewart J. Levy
*Assistant Examiner*—Joseph W. Roskos
*Attorney, Agent, or Firm*—Learman & McCulloch

[57] ABSTRACT

A method and apparatus for measuring the surface tension of a fluid wherein standing circular capillary waves are produced by spectral excitation of the fluid and the spectral function is determined from the measurement signal corresponding to the intensity of reflected light within a selected frequency range. Such a method is distinguished by its independence of external disruptive influences and its simplicity of being automated.

19 Claims, 12 Drawing Figures

METHOD AND APPARATUS FOR MEASURING AND/OR MONITORING THE SURFACE TENSION OF A FLUID

The invention relates to a method and apparatus for measuring and/or monitoring the surface tension of a fluid.

BACKGROUND OF THE INVENTION

The surface tension of many organic substances is lowered when the substances are dissolved in water. By measuring the surface tension, therefore, it is possible to determine the presence and the quantity of certain organic substances in the water.

One practical application of this method is in controlling the moistening agent in offset printing with the aid of surface-active substances. For use in process engineering the surface tension must be determined using measuring techniques with the aid of a sensor.

In a method developed by the applicants and disclosed in German Offenlegungsschrift No. 32 01 410 a circular region of the surface of the fluid is excited to oscillation so that a system of circular standing capillary waves is produced the occurrence of which is determined by measuring the intensity of a light beam reflected from the surface of the fluid.

The object of the present invention is to develop this method further so that it facilitates a particularly simple, automatic and largely maintenance-free operation and in which the measurement is very insensitive to vibration. The latter characteristic is particularly important for practical applications since the measurement must be made in the immediate proximity of running printing machines.

SUMMARY OF THE INVENTION

The surface tension of a fluid is measured or monitored by the spectral excitation of a circular region of the fluid by means of an oscillation generator. There are thus produced standing, circular capillary waves from which a light ray may be reflected. The spectral function is determined by measurement of a signal corresponding to a selected frequency of the reflected light ray.

THE DRAWINGS

Figure 3A:
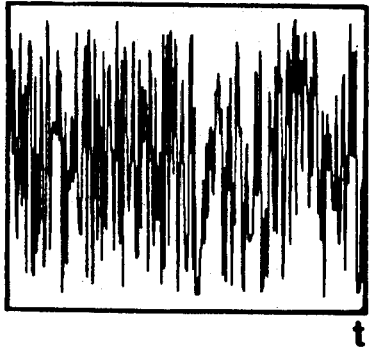
Figure 3B:
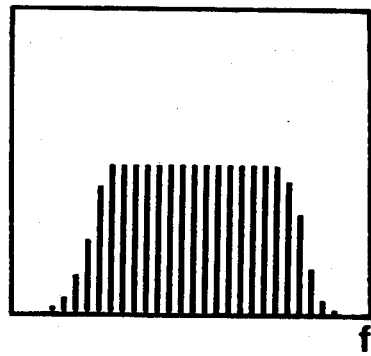
Figure 4A:
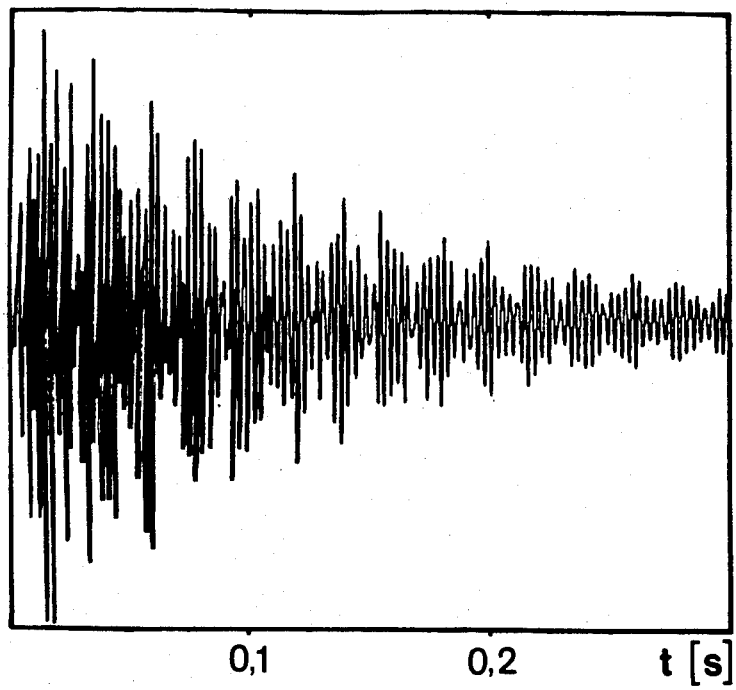
Figure 4B:
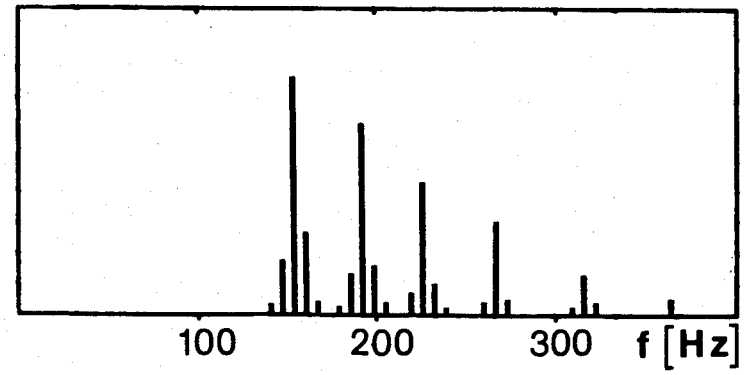
Figures 5A, 5B:
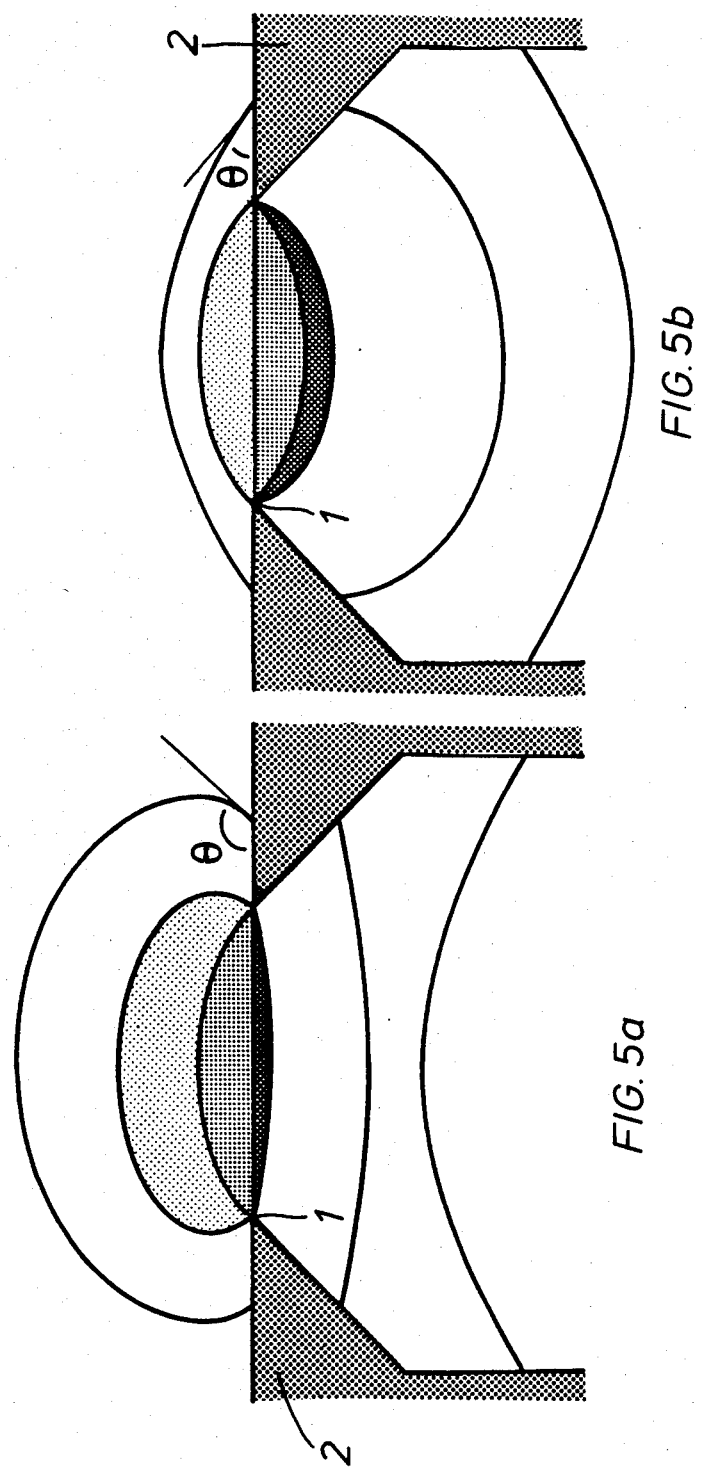
Figure 6:
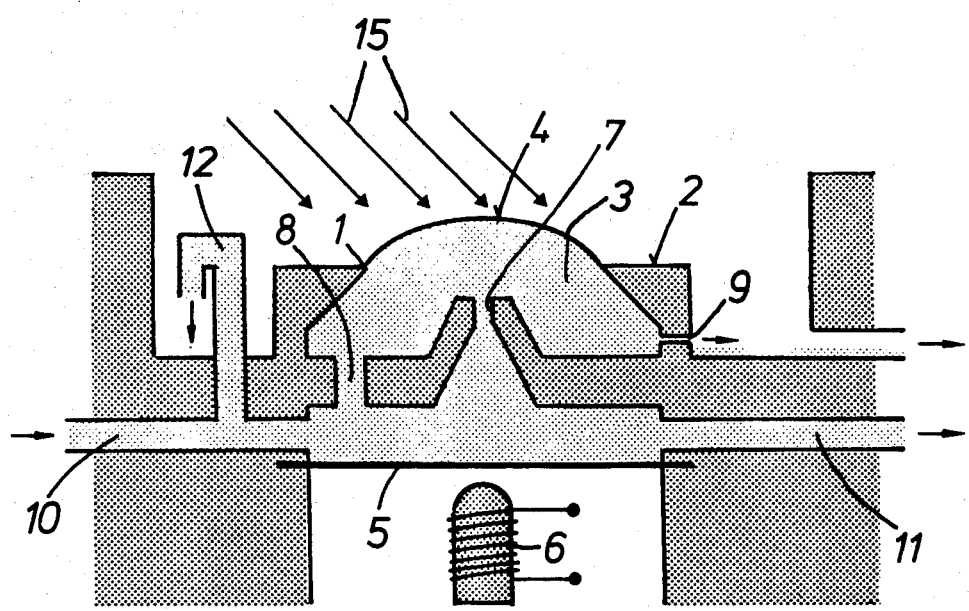
Figure 7:
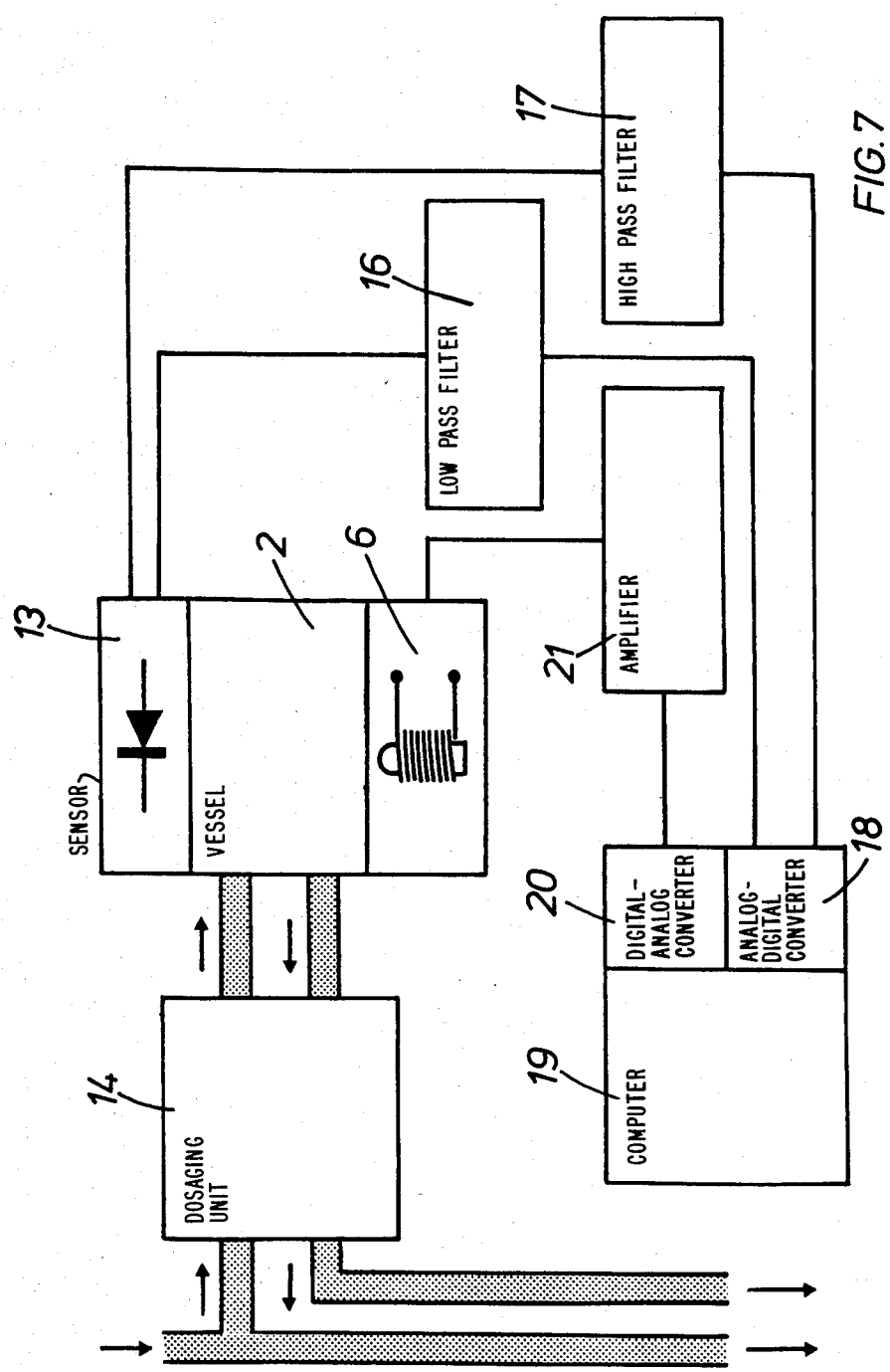

FIGS. 3a and 3b also are similar graphs indicating the same characteristics resulting from oscillation due to tape background noise;

FIGS. 4a and 4b illustrate the effects of damping on the oscillations;

FIGS. 5a and 5b diagrammatically illustrate the differences between the arcuate surfaces of water and a mixture of water and alcohol, respectively;

FIG. 6 is a diagrammatic sectional view of a vessel according to the invention; and FIG. 7 is a schematic illustration of the apparatus and the process.

DETAILED DESCRIPTION

To facilitate understanding of the principle of the method according to the invention a number of forms of excitation, as regards their time function and their spectral function, will be explained first of all with reference to FIGS. 1–4.

Figure 1A:
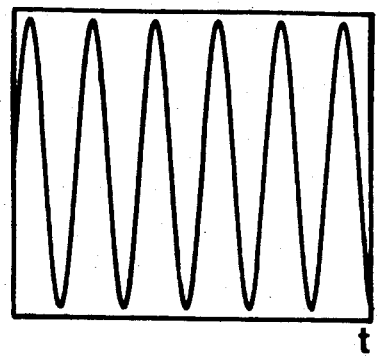
FIGS. 1a and 1b are graphs illustrating amplitude and time characteristics of a periodic oscillation and the corresponding spectral representation, respectively, of such oscillation.
Figure 1B:
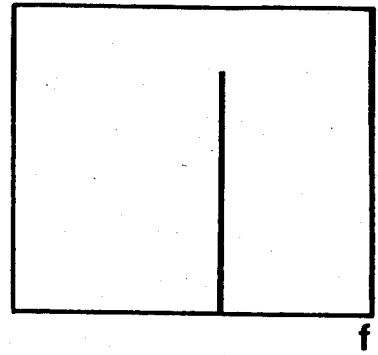

FIG. 1a shows the time function of a periodic excitation (oscillation), the amplitude of the periodic oscillation being shown in the ordinate and the time t in the abscissa. FIG. 1b shows the spectral function (frequency distribution) the abundance being shown in the ordinate and the frequency f in the abscissa. Thus, a periodic excitation according to FIG. 1a corresponds in the spectral representation of FIG. 1b to one single needle.

Figure 2A:
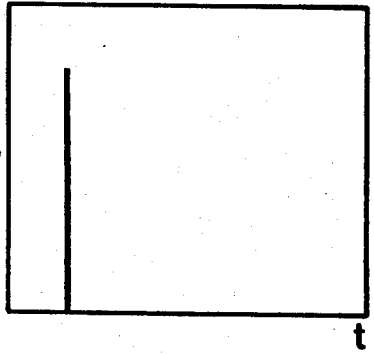
FIGS. 2a and 2b are graphs corresponding to FIGS. 1a and 1b, but illustrating the same characteristics resulting from a collision or impact oscillation.
Figure 2B:
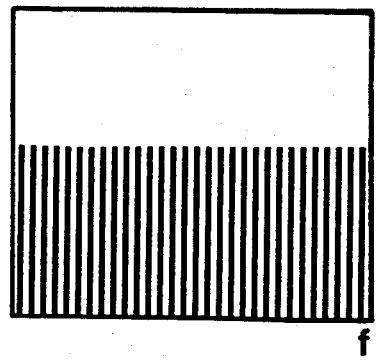

By contrast, FIG. 2a shows a collision or impact excitation as one single pulse. FIG. 2b shows the spectral function of the collision excitation as a broad frequency band having numerous needles.

A further possibility for spectral excitation is shown in FIG. 3a. Here the excitation occurs in the form of tape background noise. The spectral function of this tape background noise is shown schematically in FIG. 3b.

If the surface of a fluid is excited to oscillation in the form of standing circular capillary waves by spectral excitation (of the type shown in FIGS. 2a or 3a), then depending upon the corresponding limiting conditions the surface of the fluid can oscillate like a string only in discrete modes (fundamental tone and overtones). The time function of such damped oscillation of the surface of the fluid is shown in FIG. 4a and its spectral function is shown in FIG. 4b. Therefore the surface of the fluid acts as a filter which only accepts the appropriate frequencies of the spectral excitation.

The measurement of the surface tension of fluids by means of collision excitation of standing capillary waves proves to be completely independent of external disruptive influences, since the latter are integrated to an extent into the excitation spectrum. In contrast, in a purely periodic excitation (according to FIG. 1a), external influences can excite oscillation even when the frequency of the periodic excitation is close to the resonance frequency. In this case costly oscillation insulation of the measuring system would be necessary. The measuring method according to the invention is therefore distinguished by a high degree of insensitivity to the influence of vibrations in the surroundings.

A further advantage of spectral excitation of the fluid lies in the temporal limitation of the measuring process. This requirement is closely connected to the reproducibility of the geometry of the surface of the fluid, which will be explained in greater detail below.

In order to obtain a free surface oscillation the surface of the fluid must be subjected to fixed limiting conditions. The solid-fluid-gaseous triple point on the wall of the vessel should not move during the oscillation, since otherwise the incident ray is incompletely reflected. The surface of the fluid must therefore be "suspended" on a sharp edge or blade.

FIG. 5 shows a version which offers the possibility of achieving an even surface in the case of fluids with variable surface tension. FIG. 5a shows schematically the situation when water is used as the fluid and FIG. 5b shows the situation when a mixture of water and alcohol is used.

If the vessel 2 is completely full a convex surface is formed on the fluid which has a variable curvature (boundary angle θ) depending upon the surface tension of the fluid. The circular cutting edge 1 of the vessel 2 represents a discontinuity of the wall on which the surface of the fluid can assume different curvatures without the triple point being displaced.

The construction and the function of a measuring apparatus operating by the method according to the invention will be explained in context below by reference to FIGS. 6 and 7.

The measuring apparatus shown in FIG. 6 contains a fluid chamber 3 in a measuring vessel 2 having a circular opening at its upper end defined by the circular cutting edge 1 already referred to above. The cutting edge or blade 1 has a hydrophobic surface and encircles the convex surface 4 of the fluid when the chamber is full.

The base of the fluid chamber 3 is formed by a membrane 5. An electromagnetic impulse generator 6 is mounted a short distance below the membrane.

A nozzle 7, the axis of which extends through the centre of the chamber 3, is arranged in the fluid chamber 3 above the membrane 5 but below the fluid surface 4. The regions of the fluid chamber 3 located above and below the nozzle 7 are connected to each other by means of a lateral fluid supply channel 8. The fluid chamber 3 is also provided with a predetermined leakage drain 9 which effects a slow drawing off of the fluid.

The fluid to be studied flows in through a channel 10 and flows out through a channel 11. The delivery channel is connected to an overflow 12 which opens on a level corresponding to that of the blade 1.

The whole measuring apparatus is illustrated in a block diagram in FIG. 7.

This block diagram contains the measuring vessel 2 which is shown in detail in FIG. 6 and has the electromagnetic impulse generator 6 and a sensor 13. By means of a hydraulic relaxation oscillation a dosaging unit effects filling of the measuring vessel 2 with fluid and also its emptying. The amplitude and period of this hydraulic relaxation oscillation are advantageously adjustable in known manner.

The fluid surface 4 (cf. FIG. 6) is illuminated by a light source (not shown) from which emanate light rays 15. The light which is reflected by the fluid surface 4 is measured by the sensor 13 and modulated by the standing circular capillary waves produced on the fluid surface 4. The output signal from the sensor 13 is passed on the one hand via a low-pass filter 16 and on the other hand via a high-pass filter 17 and an analog-digital converter 18 to a computer 19. The computer 19 supplies a signal to the electromagnetic impulse generator 6 via a digital-analog converter 20 and an amplifier 21.

The measuring apparatus functions as follows:

First of all the measuring vessel 2 is filled with the fluid to be measured via the dosaging unit 14 until the fluid surface 4 exhibits a convex curvature (as shown in FIG. 6). A signal corresponding to the quantity of constant light is passed to the computer 19 via the low-pass filter 16 which allows frequencies below approximately 20 Hz to pass through. During the filling operation this quantity of constant light has a first maximum when the fluid surface is flat. By this the computer 19 recognizes that a new measuring operation is directly imminent.

When the filling of the measuring vessel 2 is completed and therefore no more fluid flows via the dosaging unit 14 into the measuring vessel 2, then the convex curvature of the fluid surface 4 is slowly reduced since some fluid continuously flows off via the predetermined leakage point 9. When the fluid surface 4 has become flat the sensor 13 determines a second maximum of the quantity of constant light for the light reflected by the surface. The computer 19 now supplies a signal to the impulse generator 6 which passes one single impulse to the membrane 5 and thus through this spectral excitation triggers the generation of standing circular capillary waves on the flat fluid surface 4.

The capillary waves occuring on the fluid surface modulate the reflected light ray. The signal picked up by the sensor 13 is delivered via the high-pass filter 17, which allows frequencies between 150 and 400 Hz to pass through, and the analog-digital converter 18 to the computer 19 and is received by the latter with a measurement frequency of, for example, 1 kHz. After approximately 0.3 s the measuring operation is ended and the computer 19 actuates the emptying of the measuring vessel 2. Therefore during this short measuring interval the geometry of the fluid surface 4 only alters to a negligible extent.

During the emptying and refilling of the measuring vessel the computer 19 calculates the spectral function of the signal with the aid of FFT (Fast Fourier Transformation). The fundamental and harmonic oscillations of the fluid surface occur according to FIG. 4b as a series of individual peaks from which the surface tension of the fluid can be determined.

For calibration of the measuring system fluids having a known, defined surface tension are used. The displacement of the frequency spectrum on variation of the surface tension is fed into the computer as a mathematical function which is determined by adaptation to the experimentally obtained values. On the basis of this function the computer can determine the surface tension of any fluids.

After completion of the calculations and the subsequent regulating operations the computer again measures the quantity of constant light of the light signal, in the course of which, in the manner described and with the aid of the first maximum of the quantity of constant light, it recognizes when the measuring vessel is again full, and begins a new measuring cycle when in the course of the slow emptying of the measuring vessel via the predetermined leakage point 9 a flat fluid surface occurs and with it a second maximum of the quantity of constant light.

The measuring system is also capable of carrying out periodic measurements in multiplex operation without external intervention as fluids are delivered one after the other to the measuring vessel 2 from different measuring points. Thus the apparatus can carry out the most varied monitoring and regulating tasks.

In the embodiment described above the spectral excitation of the fluid occurred by means of an impulse generator in the form of one single collision excitation shortly before the measuring operation.

However, it is also possible within the scope of the invention to carry out the spectral excitation of the fluid by means of a noise generator in the form of tape background noise. In the case of very strong damping of the capillary wave the electromagnetic excitation system can be applied to the membrane 5 by means of a spring and the excitation can be carried out by means of a noise generator which supplies tape background noise in the desired frequency range (in this case in the diagram of FIG. 7 the amplifier 21 is replaced by a noise generator to which a band filter is connected). Also in this case the insensitivity of the measuring system to external influences which is essential for the method according to the invention is maintained. In contrast to the impulse excitation, the noise excitation is also carried out during the measuring operation.

The internal resonances of the membrane 5 advantageously lie outside the frequency range selected for determination of the spectral function. A coated membrane is advantageously used so that in addition to corrosion resistance a very high degree of damping is also achieved.

What is claimed is:

1. In a method of measuring and/or monitoring the surface tension of a fluid wherein a circular region of the fluid surface is excited by an oscillation generator to produce standing circular capillary waves and light reflected from said fluid surface is measured the improvement wherein:
   a. the oscillation is generated by spectral excitation of the fluid; and
   b. the spectral function is determined from the measurement signal corresponding to the reflected light within a selected frequency range.

2. The method according to claim 1 wherein the spectral excitation of the fluid is achieved by an impulse generator in the form of a single collision excitation occurring shortly before the measuring operation.

3. The method according to claim 1 wherein the spectral excitation of the fluid is achieved by a noise generator in the form of tape background noise occurring during the measuring operation.

4. The method according to claim 1 wherein said fluid is contained in a chamber and wherein the spectral excitation of the fluid takes place in the centre of a membrane which forms the base of the fluid chamber.

5. The method according to claim 1 including the following features:
   a. producing a convex curvature of the fluid surface;
   b. reducing the convex curvature of the fluid surface until it becomes flat; and
   c. performing the spectral excitation and determining the spectral function when the fluid surface has become flat.

6. The method according to claim 5 including repeatedly producing and reducing the convex curvature of the fluid surfce and exciting and determining the spectral function each time the surface of said fluid becomes flat.

7. The method according to claim 1 including passing the measurement signal corresponding to the reflected light to a computer via a high-pass filter which passes frequencies in the frequency range of between 150 and 400 Hz.

8. The method according to claim 1 including passing the measurement signal corresponding to the reflected light to a computer via a low-pass filter which passes frequencies below 20 Hz.

9. Apparatus for use in measuring or monitoring the surface tension of a fluid comprising a vessel having a fluid chamber therein, said chamber having a circular opening at its upper end; means for delivering fluid to said chamber in an amount to cause its upper surface to assume a convex curvture and extend through said opening; means for producing standing capillary waves on said surface; means for illuminating said surface with light for reflection from said surface; means for receiving light reflected from said surface; means responsive to the reception of said reflected light for generating an electrical signal having a range of frequencies proportional to the intensity of the reflected light; and means for measuring the intensity of said reflected light within a selected frequency range.

10. Apparatus according to claim 9 wherein said chamber is defined by a sharp cutting edge of said vessel.

11. Apparatus according to claim 10 wherein said circular edge has a hydrophobic surface.

12. Apparatus according to claim 9 wherein said chamber has a bottom formed by a membrane.

13. Apparatus according to claim 12 wherein said membrane has an internal resonance frequency range outside said selected frequency range.

14. Apparatus according to claim 12 wherein said membrane is coated to have a high degree of damping.

15. Apparatus according to claim 9 wherein a fluid filling nozzle opens into said chamber and has its axis at the center of the chamber.

16. Apparatus according to claim 9 including means in communication with the means for delivering fluid to said chamber and forming an overflow at a level corresponding to that of said opening.

17. Apparatus according to claim 9 wherein the means for delivering fluid to said chamber includes a nozzle extending into said chamber at the center thereof and a lateral fluid channel opening into said chamber adjacent one side thereof.

18. Apparatus according to claim 9 wherein said chamber has a drain.

19. Apparatus according to claim 18 wherein said drain has a lower capacity than that of the means for delivering fluid to said chamber.

* * * * *